(12) United States Patent  
Govindasamy et al.

(10) Patent No.: US 8,856,967 B2
(45) Date of Patent: Oct. 14, 2014

(54) GLOVE WITH IMPROVED FINGER AREAS

(71) Applicant: Summit Glove Inc., Minerva, OH (US)

(72) Inventors: Baskaran Govindasamy, Subang Jaya (MY); James L. Hull, Malvern, OH (US)

(73) Assignee: Summit Glove Inc., Minerva, OH (US)

( * ) Notice: Subject to any disclaimer, the term of this patent is extended or adjusted under 35 U.S.C. 154(b) by 0 days.

(21) Appl. No.: 13/832,851

(22) Filed: Mar. 15, 2013

(65) Prior Publication Data

US 2014/0259283 A1  Sep. 18, 2014

(51) Int. Cl.
*A41D 19/00* (2006.01)
*A41D 19/015* (2006.01)
*A61B 19/04* (2006.01)

(52) U.S. Cl.
CPC .......... *A61B 19/04* (2013.01); *A41D 19/01547* (2013.01)
USPC .......................................................... 2/163

(58) Field of Classification Search
USPC ............ 2/161.7, 161.8, 163, 167, 168, 161.3, 2/159
See application file for complete search history.

(56) References Cited

U.S. PATENT DOCUMENTS

| 2,036,413 | A | * | 4/1936 | Herbruck | 2/168 |
| 3,283,338 | A | * | 11/1966 | Landau | 2/161.6 |
| 3,867,727 | A | * | 2/1975 | Povlacs | 2/167 |
| 4,441,213 | A | * | 4/1984 | Trumble et al. | 2/16 |
| 5,323,490 | A | * | 6/1994 | Yarbrough | 2/161.7 |
| 5,953,751 | A | * | 9/1999 | Kobren | 2/16 |
| 2002/0166156 | A1 | | 11/2002 | Clark et al. | |
| 2007/0245453 | A1 | | 10/2007 | Dolenak | |
| 2010/0132087 | A1 | | 6/2010 | Gait | |

FOREIGN PATENT DOCUMENTS

MY    PI 20055937    6/2007

* cited by examiner

*Primary Examiner* — Tejash Patel
(74) *Attorney, Agent, or Firm* — Sand & Sebolt

(57) ABSTRACT

A glove including a wrist region, a palm region, and digit regions. A band zone is defined in a back surface of one or more digit regions and grippingly engages a back of the user's digit received in that region. The band zone includes C-shaped elastomeric bands disposed at right angles to a longitudinal axis of the digit region. Each band extends around less than one half of the circumference of the digit region. The band zone extends from proximate the palm region to an area disposed adjacent a nail of the user's digit. A smooth zone is provided in a surface of the digit region opposite the band zone. The smooth zone is free of elastomeric bands and contacts a front surface of the user's digit. This configuration aids in gripping the user's digit while preserving tactile sensitivity therein when the glove is used for long periods of time.

20 Claims, 5 Drawing Sheets

GLOVE WITH IMPROVED FINGER AREAS

BACKGROUND OF THE INVENTION

1. Technical Field

This invention relates generally to gloves. More particularly, this invention relates to nitrile or natural rubber latex gloves. Specifically, this invention is directed to a glove which includes a series of gripping bands in regions that will fall adjacent the back of the knuckles of the user's fingers and thumb.

2. Background Information

Surgical gloves are made from relatively thin materials and have a tendency to stretch when they are worn for long periods of time. The digits regions, i.e., finger regions and thumb region, of surgical gloves are particularly prone to stretching. As the digit regions stretch, the glove begins to lose the ability to cling to or grip the user's hand and the surgeon can thereby begin to lose tactile sensitivity.

A solution to this problem has been proposed in the prior art and is disclosed in Malaysian Patent Application Serial No. PI 20055937 (Baskaran), assigned to Brightway Holdings SDN BHD of Selangor Darul Ehsan, Malaysia. The Brightway glove includes a plurality of encircling elastomeric bands formed in the digit regions of the glove, specifically in locations which will surround the user's lowermost knuckles on their fingers and thumb. The bands are provided on the internal surface of the glove, with the first band being positioned approximately midway along the length of the digit region and the last band being disposed at the base of the digit region, i.e., where the digit engages the palm region.

While the elastomeric bands aid in overcoming the tendency of the digit regions to stretch and lose contact with the user's fingers or thumb, the increased thickness around the base of the finger may be an issue when objects are gripped. Additionally, the upper part of the digit regions is still prone to stretching.

There is therefore a need in the art for a glove that has improved gripping capabilities along substantially the entire length of the user's fingers and thumb.

BRIEF SUMMARY OF THE INVENTION

A nitrile or natural rubber latex glove including a wrist region, a palm region, and digit regions. A band zone is defined in a back surface of one or more digit regions and grippingly engages a back of the user's digit received in that digit region. The band zone includes C-shaped elastomeric bands disposed at right angles to a longitudinal axis of the digit region. Each band extends around less than one half of the circumference of the digit region. The band zone extends from proximate the palm region to an area disposed adjacent a nail of the user's digit. A smooth zone is provided in a surface of the digit region opposite the band zone. The smooth zone is free of elastomeric bands and contacts a front surface of the user's digit. This configuration aids in gripping the user's digit while preserving tactile sensitivity therein when the glove is used for long periods of time.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

Similar numbers refer to similar parts throughout the drawings.

DETAILED DESCRIPTION OF THE INVENTION

Referring to FIGS. 1-6 there is shown a glove in accordance with the present invention, generally indicated at 10. Glove 10 is configured to be worn on a user's left hand. It will be understood that a glove configured to be worn on a right hand of a user will be a mirror image of the glove 10 illustrated herein. Glove 10 preferably is fabricated from nitrile or natural rubber latex; although other materials are also possible.

Figure 1:
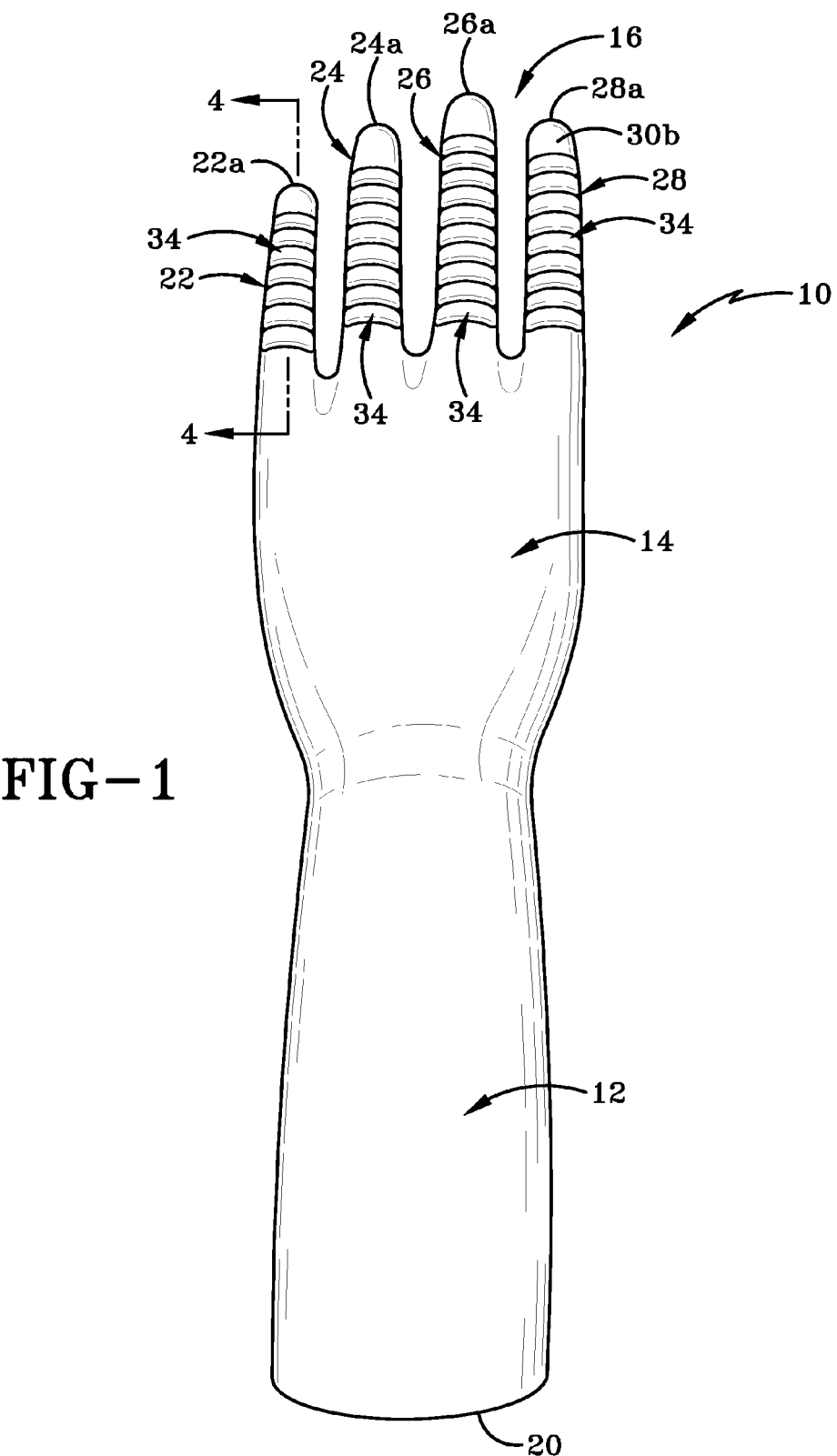
FIG. 1 is a rear elevational view of a left-handed glove in accordance with the present invention.
Figure 2:
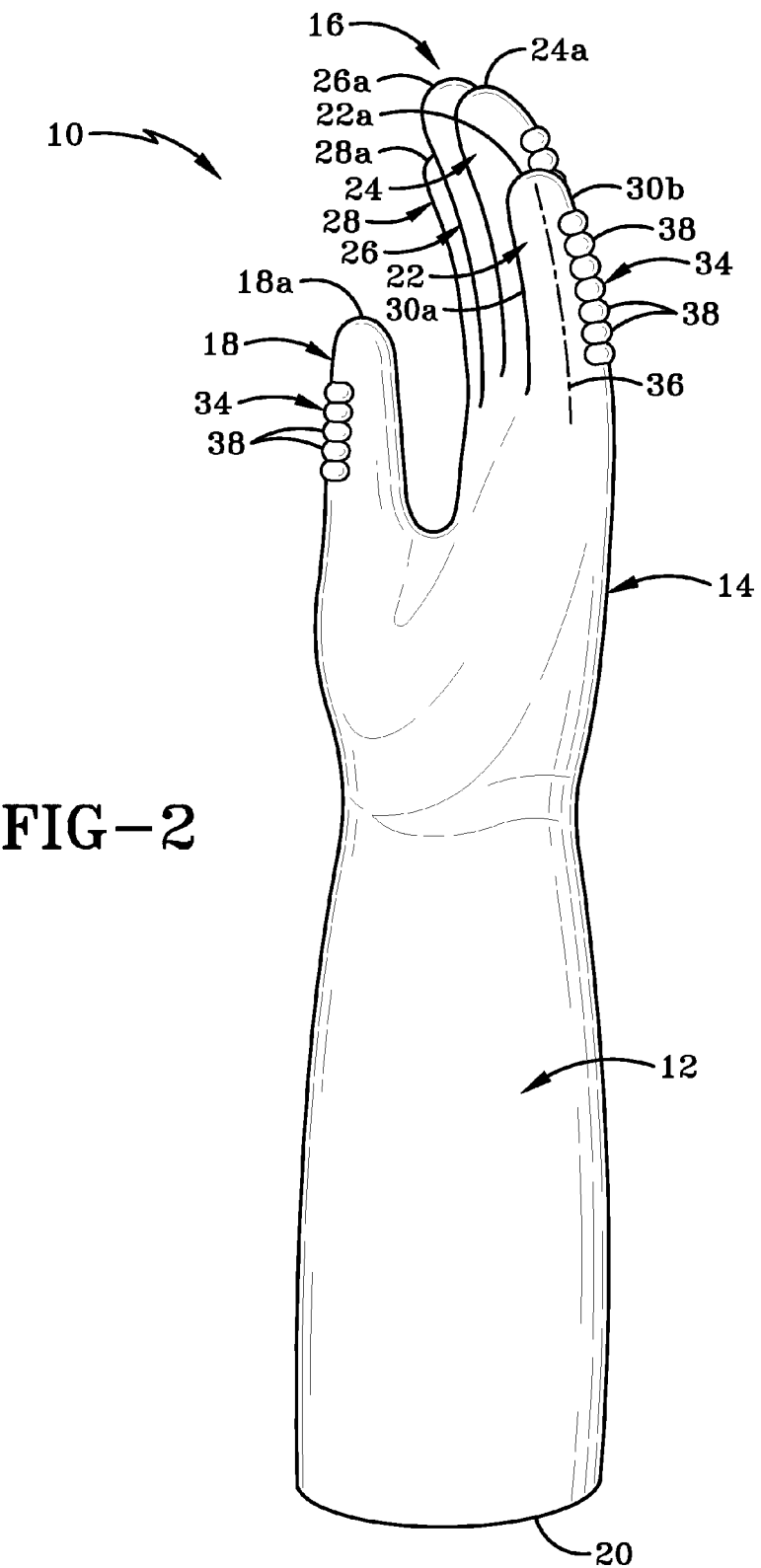
FIG. 2 is a left side view of the glove of FIG. 1.
Figure 3:
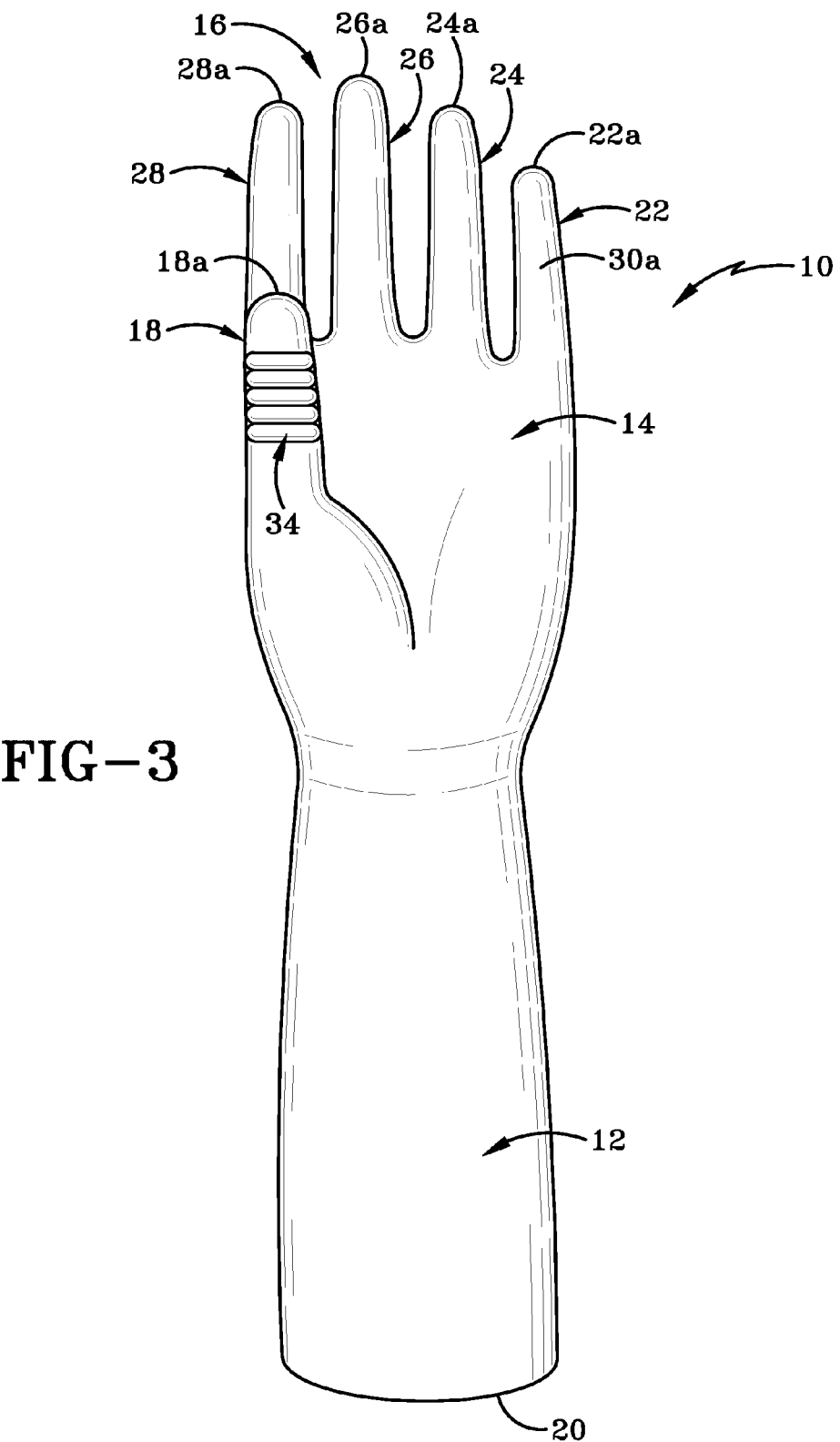
FIG. 3 is a front elevational view of the glove of FIG. 1.

Glove 10 includes a wrist region 12, a palm region 14, a finger region 16, and a thumb region 18 (FIG. 2). Wrist region 12 is configured to encircle the wrist and a portion of the forearm of a user. Wrist region 12 includes an edge 20 which defines an opening (not shown) through which the user will insert their hand. The length of wrist region 12 may be varied to be relatively short and configured to simply provide a cuff on the bottom of the palm region 14, or relatively long and configured to reach almost to the user's elbow, or may be somewhere between a cuff and elbow length.

Palm region 14 is configured to encircle both the back and front of the users hand and extends from the wrist region 12 through to the digit region, specifically to the base of finger region 16 and thumb region 18.

The finger region 16 includes a little finger region 22, a ring finger region 24, a middle finger region 26 and an index finger region 28 originated in and integral with palm region 14. Furthermore, each of the little, ring, middle, and index finger regions 22-28 terminates in a tip 22a, 24a, 26a, 28a, respectively, that is remote from palm region 14. Similarly, thumb region 18 originates in and is integral with palm region 14 and terminates in a tip 18a which is remote from palm region 14.

Each of the finger regions 16 and thumb region 18 are similarly configured with respect to being improved in accordance with the present invention. Thus, these improved digit regions are able to readily grip the users finger or thumb while still being able to flex and bend easily. The following description will focus on little finger region 22 but it will be understood that the description applies equally to each of the ring, middle and index finger regions 24, 26, 28 and thumb region 18.

Figure 4:
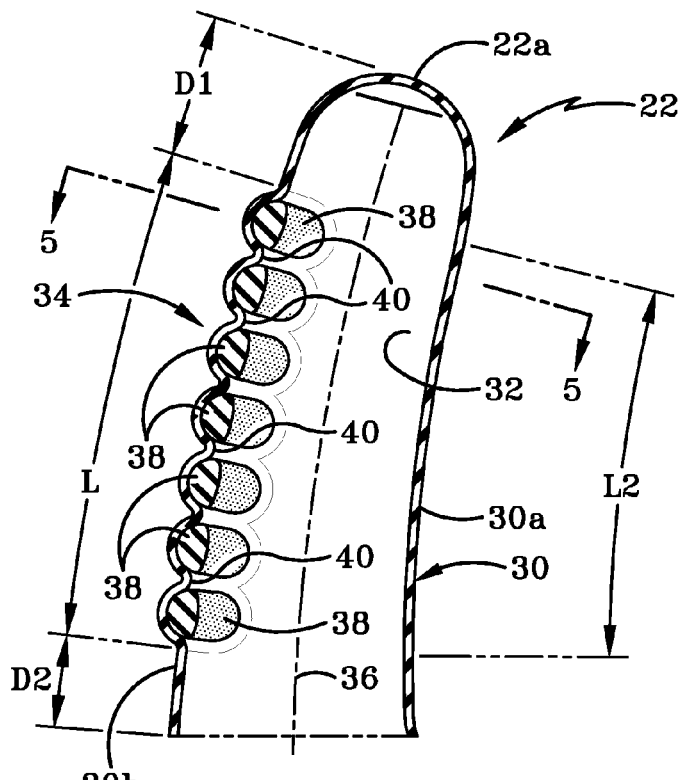
FIG. 4 is a cross-sectional left side view of the glove taken along line 4-4 of FIG. 2.
Figure 5:
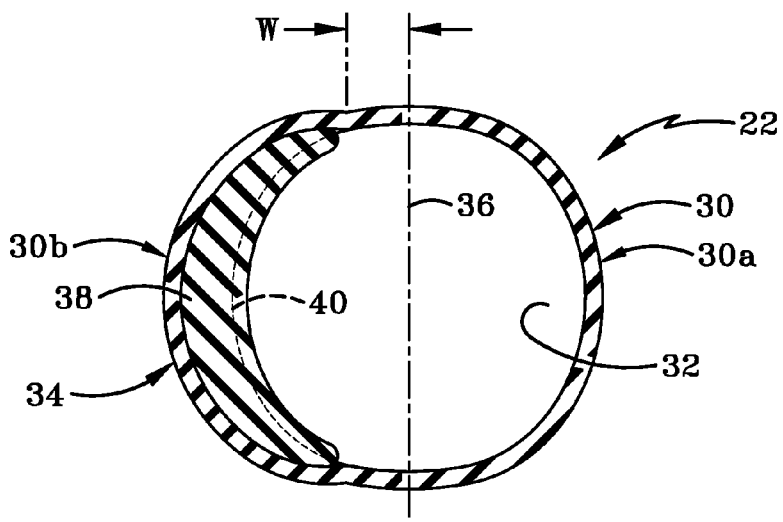
FIG. 5 is an enlarged cross-sectional top view of the little finger taken along line 5-5 of FIG. 4 and showing a portion of a band and a portion of a trough formed therein.
Figure 6:
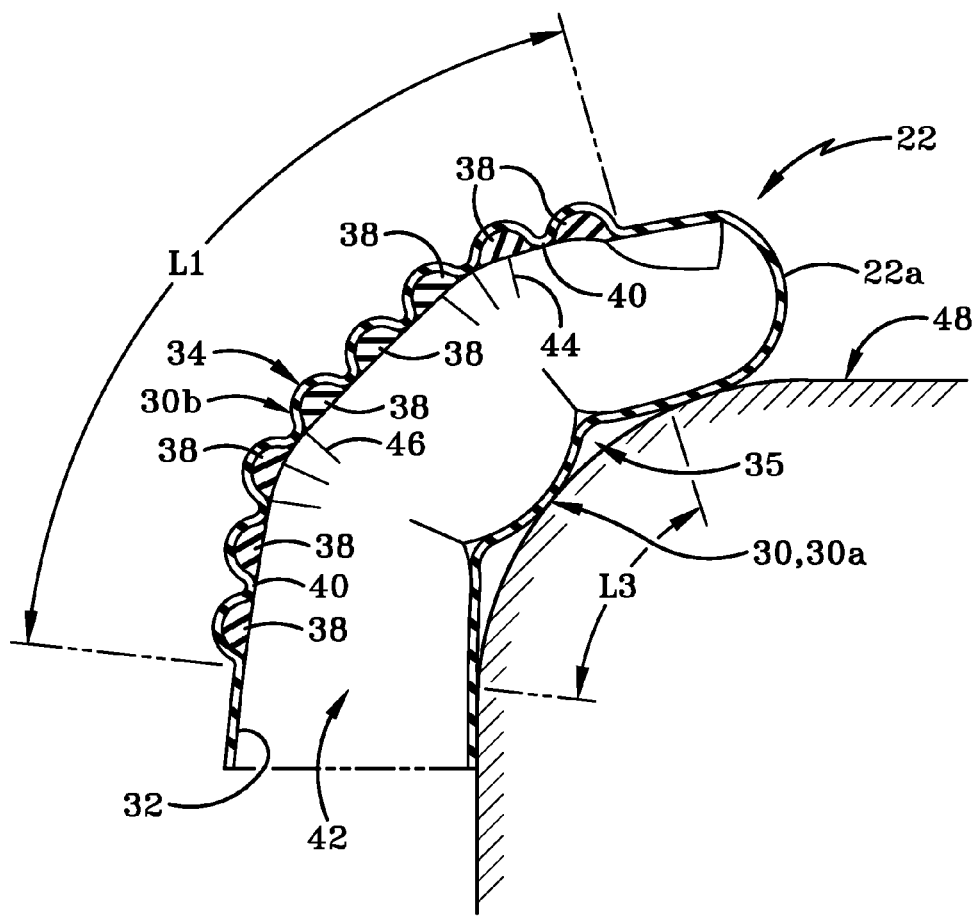
FIG. 6 is a cross-sectional left side view of the little finger region shown with the user's little finger disposed therein and bent at both knuckles, thereby stretching out the material of the band zone.

Referring to FIGS. 4-6, little finger region 22 comprises a generally cylindrical peripheral wall 30 which is generally circular to elliptical in cross-sectional shape. Peripheral wall 30 bounds and defines an interior cavity 32 into which the user's little finger 42 (FIG. 6) is received. (The user's little finger 42 includes an upper knuckle 44, a lower knuckle 46, a fingernail 47 and front and rear surfaces which are not numbered.) Peripheral wall 30 of little finger region 22 has a front surface 30a and a back surface 30b which extend therebetween. Each of the front and back surfaces 30a, 30b are generally C-shaped in cross-section. Front surface 30a is configured to be disposed adjacent the front surface of the user's little finger 42 and along a front portion of each of the left and right sides thereof. Back surface 30b is configured to be disposed adjacent the rear surface of the user's little finger 42 and a rear portion of each of the left and right sides thereof.

Still referring to FIGS. 4-6, in accordance with a specific feature of the present invention, rear surface 30b of little finger region 22 is provided with a band zone 34 therein. Band zone 34 is provided to grippingly engage the rear surface of the user's little finger 42, as will be hereafter described. Band zone 34 originates a distance "D1" from tip 22a of little finger region 22 and terminates a distance "D2" from palm region 14a. In accordance with a specific feature of the present invention, band zone 34 is longitudinally sufficiently long enough to extend from adjacent an upper region of upper knuckle 44 (FIG. 6) on the user's little finger 42 to adjacent a lower region of the lower knuckle 46. FIG. 4 shows the little finger region 22 in a straightened position and the overall length of band zone 34 is indicated by the reference character "L". Length "L" is approximately two-thirds to three-quarters of the total length of little finger region 22, where the total length thereof is measured from tip 22a to palm region 14. Thus, band zone 34 extends for the majority of the length of little finger region 22. The area of little finger region 22 between tip 22a and the band zone 34 will be disposed adjacent the user's fingernail 47. Thus, when glove 10 is worn on the user's hand, band zone 34 will grippingly engage substantially the entire length of the flesh portion of the back surface little finger 42.

In accordance with yet another feature of the present invention, band zone 34 comprises a plurality of elastomeric bands 38 which are provided on the interior surface of little finger region 22 and project for a distance into cavity 32. Each band 38 is generally C-shaped when little finger region 22 is viewed in cross-section (FIG. 5). Little finger region 22 has a longitudinal axis which extends from tip 22a to palm region 14. Each band 38 is disposed generally at right angles to this longitudinal axis. Adjacent bands 38 are separated from each other by a shallow trough 40. Each bands 38 extends around less than one half of the circumference of peripheral wall 30 as may be seen in FIG. 5. Specifically, each side edge of each band 38 originates and terminates a distance "W" (FIG. 5) away from the longitudinal midline 36 of the sides of little finger region 22. An interior surface of each band 38 is disposed in cavity 32 and is positioned for contact with the rear surface and a rear portion of each of the left and right sides of the user's little finger 42.

In accordance with another specific feature of the present invention, front surface 30a of little finger region 22 is substantially smooth along the entire length thereof, where the length is measured from tip 22a to palm region 14. In other words, front surface 30a comprises a smooth zone 35 which is free of elastomeric bands. Smooth zone 35 is disposed opposite band zone 34. Thus, the interior surface of smooth zone 35 is in direct contact with the front surface of little finger 42 when received in cavity 32.

FIG. 6 shows a part of glove 10 in use. Specifically, this figure shows the user's little finger 42 disposed within cavity 32 of little finger region 22 with both upper knuckle 44 and lower knuckle 46 bent in a way that enables the user to hold an object 48 using their hand. The back surface of little finger 42 is in direct contact with an interior surface of the plurality of bands 38 of band zone 34. Band zone 38 originates proximate the bottom of fingernail 47 and extends beyond a lower region of lower knuckle 46. The front surface of little finger 42 is in direct contact with the interior surface of smooth zone 35.

When little finger 42 bends in this fashion, each band 38 of band zone 34 stretches longitudinally and becomes flattened, thus increasing the overall length of each band 38 and therefore the overall length of band zone 34. Additionally, the curvature of each trough 40 is also flattened out. This overall increased length of band zone 34 in the expanded state is shown in FIG. 6 by the reference character "L1". "L1" is longer than "L" (FIG. 4). Thus, when little finger 42 is bent a greater surface area of band zone 34 contacts the back surface of little finger 42, increasing the gripping engagement therewith. This expanded state of band zone 34 allows the little finger 42 to easily bend at both knuckles while maintaining gripping contact with the back surface and parts of the sides of the user's little finger 42.

At the same time, the smooth zone 35 on front surface 30a becomes slightly wrinkled by the bending little finger 42. FIG. 4 shows the original length of the smooth zone 35 as being of a size "L2". When little finger 42 is bent at both upper and lower knuckles 44, 46, the overall length of the smooth zone 35 is reduced in size to "L3". Because bands 38 terminate a distance away from smooth zone 35 and generally away from the front portions of the sides of little finger region 22, there is substantially no excess build-up of the material of little finger region 22 as the little finger 42 bends. Thus, the bending of little finger 42 is not hampered. Additionally, because only front surface 30a separates little finger 42 from object 48, the tactile sensitivity of the user's little finger 42 is preserved. Still further, the provision of bands 38 only in band zone 34 along back surface 30b tends to create a pulling force on the sides of little finger region 32 and on smooth zone 35. This pulling force increases when little finger 42 is bent and thereby keeps the material of smooth zone 35 in close contact with the front of little finger 42, thereby further preserving the tactile sensitivity of the user's finger 42 even as glove 10 tends to stretch through a long period of use.

It will be understood that in thumb region 18, band zone 34 will originate in a region that will be disposed adjacent a bottom end of the nail on the user's thumb and will terminate proximate palm region 14. In other words, band zone 34 on thumb region 18 will extend for approximate two-thirds to three-quarters of the length of thumb region 18. Band zone 34 furthermore will include a plurality of bands 38 which grippingly engage the back of the user's thumb (not shown) and rear portions of the sides thereof. Thumb region 18 will further include a smooth zone that is disposed opposite band zone 34 and will abut the front of the user's thumb. Thus, the band zone 34 will function in substantially the same manner in thumb region 18 as it does in finger regions 16.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A glove comprising:
   a wrist region defining an opening therein and through which a user's hand is inserted into the glove;
   a palm region extending outwardly from a first end of the wrist region;
   a plurality of digit regions extending outwardly from a first end of the palm region remote from the wrist region; wherein each digit region originates at an upper end of the palm region and extends for a distance outwardly away therefrom and terminates in a tip; and wherein each digit region includes a longitudinal axis which extends between the tip and the upper end of the palm region; and a band zone defined in only a back surface of one or more of the plurality of digit regions of the glove; wherein the band zone originates a distance away from the upper end of the palm region; and wherein the band zone comprises at least two spaced-apart bands adapted to grip the back of the user's digit received in the one of the one or more digit regions; and the at least two bands are disposed generally at right angles to the longitudinal axis; and wherein said band zone includes a gripping surface adapted to grippingly engage a back of a user's digit received in the one of the one or more digit regions.

2. The glove as defined in claim 1, wherein each of the one or more digit regions includes a peripheral wall having a cross-sectional circumference; and wherein the band zone extends around less than half of the circumference of the peripheral wall of the one of the one or more digit regions.

3. The glove as defined in claim 1, wherein the band zone is generally C-shaped in cross-section.

4. The glove as defined in claim 1, wherein the digit regions are finger regions, and each finger region has two spaced apart areas adapted to be disposed adjacent a top knuckle and a middle knuckle on the user's finger that will be received in that finger region; and both of the spaced apart areas are disposed remote from the upper end of the palm region and the bottom knuckle on the users finger; and wherein the band zone in the one of the one or more finger regions extends along the back surface of the peripheral wall thereof and includes both of the spaced apart areas.

5. The glove as defined in claim 1, wherein each digit region has a length defined between the tip of the digit region and the upper end of the palm region of the glove; and wherein the band zone on the one of the one or more digit regions extends for approximately two-thirds to three-quarters of the length thereof.

6. The glove as defined in claim 1, wherein each digit region defines an interior cavity into which one of the user's digits is received; and wherein the at least two bands are made of an elastomer and project for a distance into the interior cavity of the one of the one or more digit regions.

7. The glove as defined in claim 1, wherein the at least two bands are generally C-shaped when viewed from the tip of the one of the one or more digit regions.

8. The glove as defined in claim 1, wherein the digit region is a thumb region and the band zone is adapted to be disposed adjacent the back of the user's thumb which is received in the thumb region; and wherein the band zone originates at a position adapted to be disposed adjacent a bottom end of the nail on the user's thumb and terminates proximate the upper end of the palm region; and wherein the band zone on the thumb region is adapted to grippingly engage the back and rear portions of the sides of the user's thumb.

9. The glove as defined in claim 8, wherein the band zone includes at least two elastomeric bands adapted to contact the back and rear portions of the sides of the user's thumb.

10. The glove as defined in claim 2, wherein the one of the one or more digit regions further includes a smooth zone disposed opposite the band zone in the peripheral wall; and wherein the smooth zone is substantially free of elastomeric bands which project into the interior cavity; and wherein the smooth zone is adapted to be disposed adjacent a front surface and front portions of the side surfaces of the user's digit received in the one or more digit regions.

11. The glove as defined in claim 1, wherein the band zone includes a plurality of alternating gripping bands and troughs.

12. The glove as defined in claim 11, wherein each of the plurality of gripping bands and each of the plurality of troughs are disposed substantially at right angles to the longitudinal axis of the one of the one or more digit regions.

13. The glove as defined in claim 12, wherein each of the gripping bands has a width measured from a first adjacent trough to a second adjacent trough; and wherein the width of each of the gripping bands is adapted to increase in size when the user's digit is bent; and is adapted to decrease in size when the user's digit is straightened.

14. The glove as defined in claim 1, wherein a first side of the band zone originates a spaced distance inwardly from a longitudinal midline of a first side of the one of the one or more digit regions; and a second side of the band zone terminates a spaced distance inwardly from a longitudinal midline of a second side of the one of the one or more digit regions.

15. The glove as defined in claim 1, fabricated from nitrile or natural rubber latex.

16. A glove comprising:
a wrist region defining an opening therein and through which a user's hand is inserted into the glove;
a palm region extending outwardly from a first end of the wrist region;
a thumb region extending outwardly from a first end of the palm region remote from the wrist region;
a plurality of finger regions extending outwardly from the first end of the palm region adjacent the thumb region; and
a band zone defined in only a back surface of each of the thumb region and the plurality of finger regions; wherein said band zones each include a plurality of gripping surfaces adapted to grippingly engage a back of a user's thumb or finger received in the associated thumb region or finger regions.

17. The glove as defined in claim 16, wherein the band zone comprises a plurality of elastomeric bands that are disposed generally at right angles to a longitudinal axis of the associated one of the thumb region or finger regions and the plurality of elastomeric bands originate a distance outwardly away from an upper end of the palm region of the glove.

18. The glove as defined in claim 17, wherein each of the thumb region and finger regions includes a generally cylindrical peripheral wall that has a circumference; and wherein each band extends around less than one half of the circumference of the associated one of the thumb region or finger regions.

19. The glove as defined in claim 16, wherein the band zone terminates in an area that is adapted to be disposed adjacent a nail of the user's thumb or finger received in the associated one of the thumb region and finger regions.

20. The glove as defined in claim 16, further comprising a smooth zone disposed in a surface of the associated one of the thumb region and finger regions opposite the band zone; and wherein the smooth zone is substantially free of elastomeric bands and is adapted to contact a front surface of the user's thumb or fingers.

* * * * *